United States Patent [19]

McCormick et al.

[11] Patent Number: 5,176,655
[45] Date of Patent: Jan. 5, 1993

[54] DISPOSABLE MEDICAL NEEDLE AND CATHETER PLACEMENT ASSEMBLY HAVING FULL SAFETY ENCLOSURE MEANS

[75] Inventors: William McCormick, Carlisle; Jacob B. Blecher, Lexington; Miles C. O'Donnell, Andover, all of Mass.

[73] Assignee: MBO Laboratories, Inc., North Chelmsford, Mass.

[21] Appl. No.: 610,583

[22] Filed: Nov. 8, 1990

[51] Int. Cl.⁵ ............................................. A61M 5/32
[52] U.S. Cl. .................................. 604/198; 604/192; 604/263
[58] Field of Search ............... 604/197, 162, 167, 192, 604/198, 263

[56] References Cited

U.S. PATENT DOCUMENTS

| | | | |
|---|---|---|---|
| 3,709,223 | 1/1973 | Macalalad | 604/162 |
| 4,775,369 | 10/1988 | Schwartz | 604/198 |
| 4,795,432 | 1/1989 | Karczmer | 604/198 |
| 4,804,371 | 2/1989 | Vaillancourt | 604/198 |
| 4,863,435 | 9/1989 | Sturman et al. | 604/198 |
| 4,887,998 | 12/1989 | Martin et al. | 604/198 |
| 4,915,697 | 4/1990 | DuPont | 604/263 |
| 4,917,672 | 4/1990 | Terndrup et al. | 604/192 |
| 4,935,012 | 6/1990 | Magre et al. | 604/192 |
| 4,943,281 | 7/1990 | Kothe | 604/192 |
| 4,978,344 | 12/1990 | Dombrowski | 604/198 |
| 5,049,136 | 9/1991 | Johnson | 604/198 |

Primary Examiner—C. Fred Rosenbaum
Assistant Examiner—Ronald Stright, Jr.
Attorney, Agent, or Firm—Low and Low

[57] ABSTRACT

A disposable medical needle assembly having unique insertion and removal means from tissue, including means for fully shielding the used or contaminated needle from hazardous access or exposure. Various such means are disclosed in cooperation with needle guide and manipulation means.

The assembly may also be utilized in conjunction with catheter placement, blood collection, and like purposes, while maintaining full and automatic safety shielding of the needle after use.

22 Claims, 11 Drawing Sheets

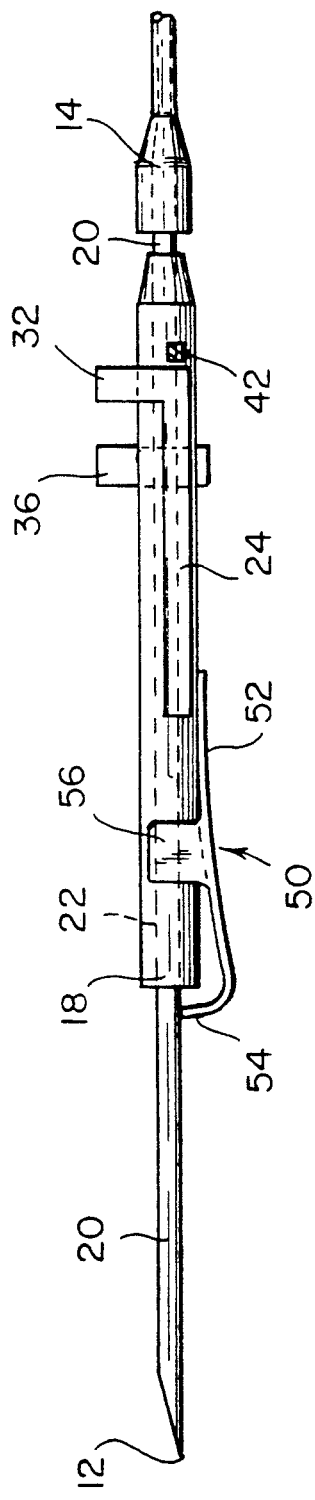
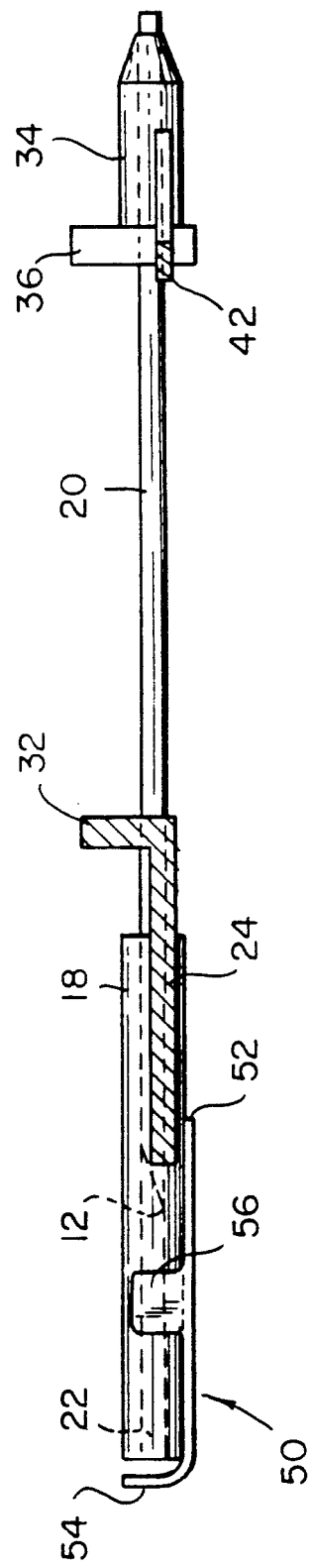

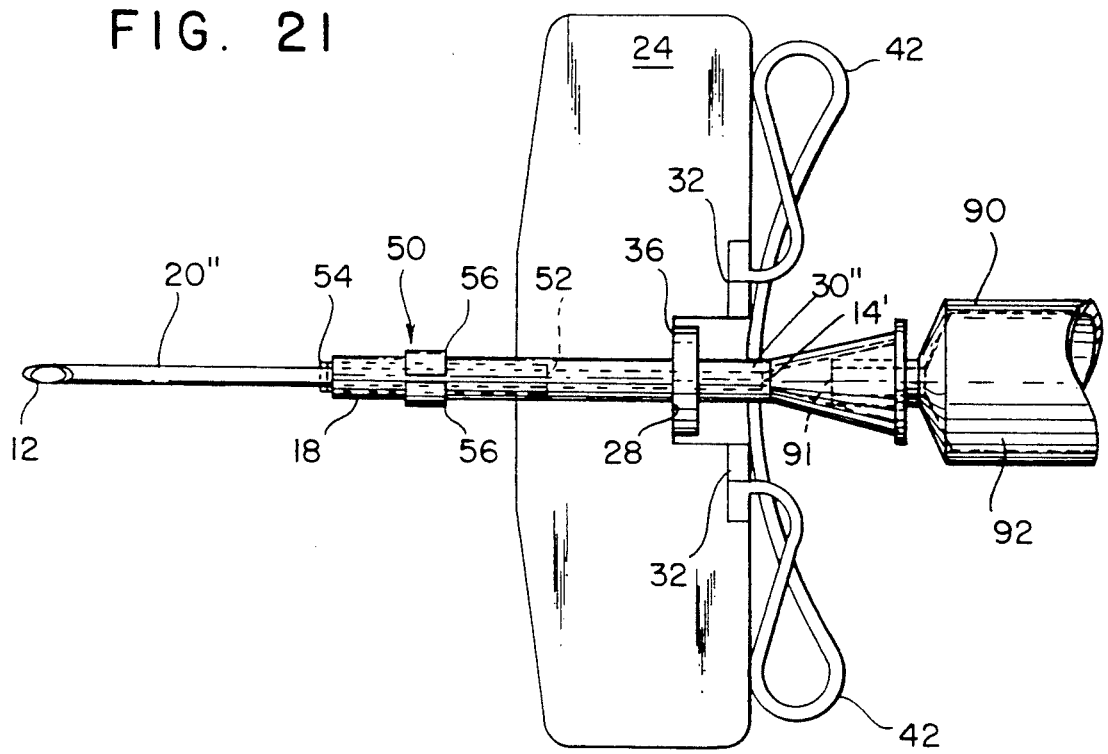
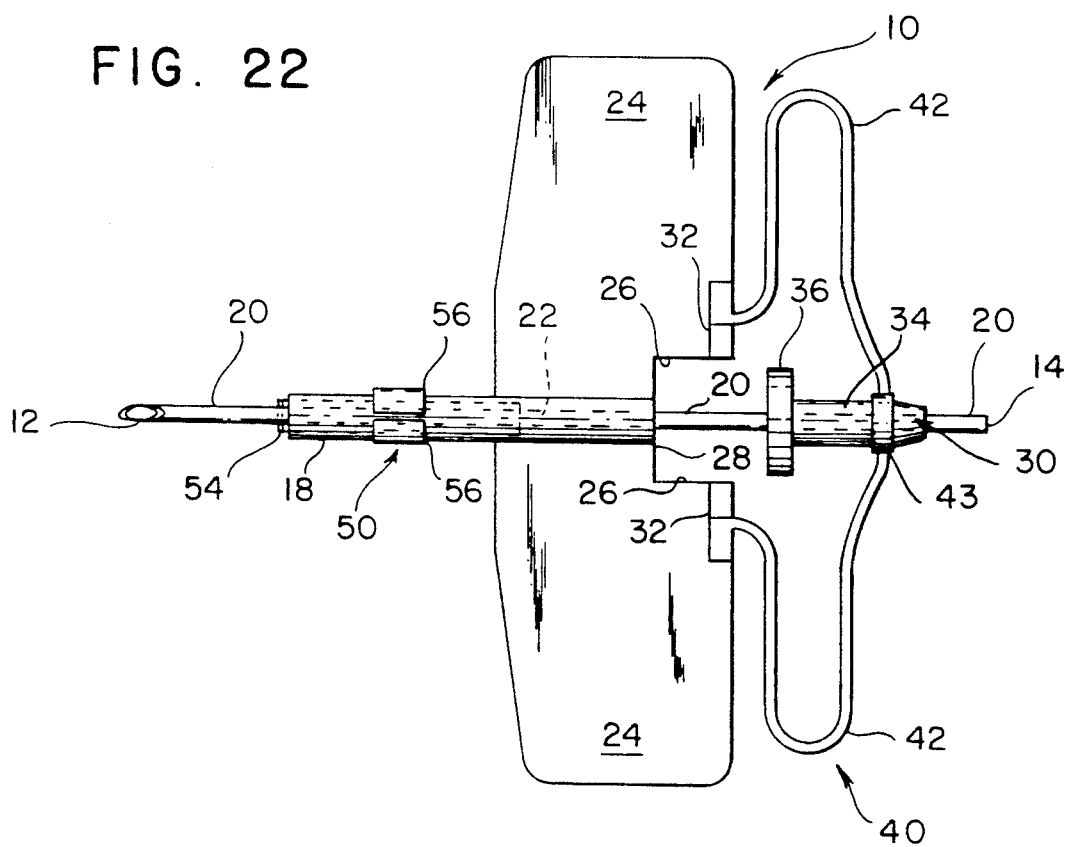

DISPOSABLE MEDICAL NEEDLE AND CATHETER PLACEMENT ASSEMBLY HAVING FULL SAFETY ENCLOSURE MEANS

BACKGROUND OF THE INVENTION

In recent years there has been considerable research and development with respect to single-use disposable needles or needle stylets for intravenous and like use to minimize the hazards of contamination from reused needles, as well as to obviate the time-consuming, labor intensive, and expensive necessity of effective cleaning, sterilization, and repackaging of reuseable needles.

While single-use throwaway needles admirably eliminate the adverse aspects of cleaning of and contamination from reused needles, this has resulted in newer problems with respect to unintended access to and danger from the used throwaway needle. The hazards include inadvertent contact with or skin rupture from a previously used and contaminated needle during intended and proper handling thereof by healthcare personnel, as in collection and disposal thereof.

With increasing concerns of potentially debilitating or fatal infections of healthcare workers or others by accidental or even deliberate needlestick injuries from used intravenous needles variously contaminated as with tissue residue of patients with AIDS virus, hepatitis B virus, or other pathogens, a number of efforts have been made to devise means for shielding or otherwise rendering inaccessible a used needle.

In providing such protection again contact with a used needle, there is an inherent practical conflict with ease and economy of manufacture, and ease of needle usage, including insertion and withdrawal. In like manner, while a simplified shielding means may not adversely impact upon manufacture and use, sacrifice is made in convenience and reliability of contamination shielding.

Illustrative devices known in the art include that of European Patent Application 0314470, published May 3, 1989, owned by Menlo Care Inc. of Palo Alto, Calif. The same is intended for use only as an IV catheter placement system, including a laterally winged catheter insertion means and a completely separate extractor assembly into which the contaminated needle point is withdrawn after use. The several components are complex of fabrication and in use, and do not provide facile, reliable means for shielding a needle.

U.S. Pat. No. 4,790,828 to Dombrowski et al deals with a self-capping needle wherein a needle cap is connected or tethered to the needle in a difficultly fabricated and handled assembly.

Other assemblies seeking to protect or shield a needle or stylet after use are typified by U.S. Pat. Nos. 4,676,783 and 4,781,692 to Jagger et al, which while theoretically useful, present manufacture and manipulative difficulties.

BRIEF SUMMARY OF THE INVENTION

It is an object of the present invention to provide a readily manufactured and easily used assembly in association with an IV needle whereby the needle is safely shielded for disposal in a reliable and virtually fail-proof manner.

In accordance with the invention, the safely disposable intravenous needle assembly includes several cooperatively associated components utilized in conjunction with a needle, namely: (1) guide means for slidably receiving a needle cannula or needle stylet, and within which guide means the used, contaminated needle is to be received for safety shielding after use; (2) manipulating means affixed to the needle to effect safe enclosure thereof; (3) interengageable means provided on the guide means and manipulating means to facilitate insertion and safe withdrawal of the needle in intravenous use.

Further, the guide means uniquely includes and carries a needle point blocking or shielding device automatically operative upon withdrawal of the used or contaminated needle into the guide means. The point shield may partake of several forms.

Adjunctively thereto, the guide means and manipulative means are interconnected by flexible and resilient means to facilitate unit-handled manufacture of the assembly as well as to control safe needle positioning within and without the guide means.

In a further form of the invention is provided a soft over-the-needle catheter device which is disposed on the needle during insertion and remains in place in the blood vessel after withdrawal of the needle. In like manner, other forms of this invention embrace utilization with blood collection systems and hypodermic needle syringe devices.

The guide means, of the invention, comprises a central tube having a bore or passageway therethrough for reception and sliding movement of a needle therein. The guide means further includes wing-like sections extending laterally from the central tube, which wings are preferably molded integrally with the central tube and are flexible with respect thereto. The operation of the device in shielding the needle after use will be set forth hereinafter, but it is noted that as part thereof, the needle will be fully withdrawn into the tubular passageway with no portion of the needle distal end projecting therefrom.

Means are provided to assure positive retention of the needle distal end within the guide member and protection from any hazard of an exposed needle tip. To this end, in a preferred form, the tubular member carries a guard device in the nature of a leaf spring which is mounted at its proximate end on the tubular member and at its distal end is provided with a needle blocking plate. The spring device as mounted on the tube is tensioned to project the blocking plate in front of the passageway at the tube distal end, but is unable to do so by projection of the needle therefrom prior to in use, during which the blocking plate is spring-urged to bear against the needle.

The distal pointed end of the needle extends from the tube, and the rearward proximal portion of the needle carries the manipulating means, namely a base member receiving the needle therethrough to which it is affixed, whereby manual movement of the base member will also move the needle. As is evident, the base member and the tubular passageway are axially aligned, wherein the manipulating means is disposed rearwardly of the guide means.

Interconnection and separation limit means are provided between the guide means and the manipulating means in the form of a resilient loop or strap, which is preferably integrally formed therewith. Accordingly, the same serves as a restraint to rearward or separating movement of the manipulating member with respect to the guide member as well as enables the unit molding and handling of the guide member and manipulating member.

Interengagement means are provided in the nature of flanges on the base member of the manipulating member and on the flexible wings of the guide member, whereby upon flexure thereof, the interengaging means become substantially axially aligned. At such time, after the base member of the manipulating is advanced initially to extend the needle point distally from the guide member, with the wings flexed together to guide the needle during insertion and to stabilize the assembly, upon engagement of the manipulating member with the guide member in this manner, the needle, guide member and manipulating member move as one unit in subcutaneously inserting the needlepoint.

After appropriate intravenous or other operations are performed through the needle, the needle is withdrawn from the tissue and safely secured. To this end, the flexible wings are held stationary and the guide member is held abutting the skin needle insertion site manipulating member withdrawn in a proximate direction, thereby retracting the needle and needlepoint into the tubular bore of the guide member. As the needle tip passes fully into the bore, the restraint against the leaf spring blocking plate is eliminated, and the blocking plate snaps transversely over the tubular member to effectively seal the end of the bore and thereby preclude any likelihood of the contaminated needle tip from emerging. Other safety means are set forth, all blocking any emergence of the contaminated tip from the guide member.

Further, the needle cannot be fully withdrawn in a rearward direction from the bore inasmuch as the dimensioning of the interconnecting restraining loops is such that when manipulating member base member carrying the needle is in its most remote position from the guide member, the interconnecting loops have insufficient length to permit the needle to approach withdrawal from the guide member passageway. The used needle assembly may now safely be discarded in toto.

BRIEF DESCRIPTION OF THE DRAWINGS

The invention will be better understood when taken with the accompanying drawings, in which:

FIG. 4 is a side view taken on the lines 4—4 of FIG. 2; portions thereof being shown in section;

FIG. 8 is a side view taken on the lines 8—8 of FIG. 7; portions thereof being shown in section;

FIG. 21 is a to plan view of a sixth modified form of the invention for use in a hypodermic needle syringe configuration;

FIG. 22 is a to plan view similar to FIG. 1 of a seventh modified form of the invention wherein the interconnecting straps are detachably connected to the manipulating member; and, FIG. 23 is a to plan view of yet another form of the invention wherein the wings and manipulating members are altered.

DESCRIPTION OF PREFERRED EMBODIMENTS

Figure 1:
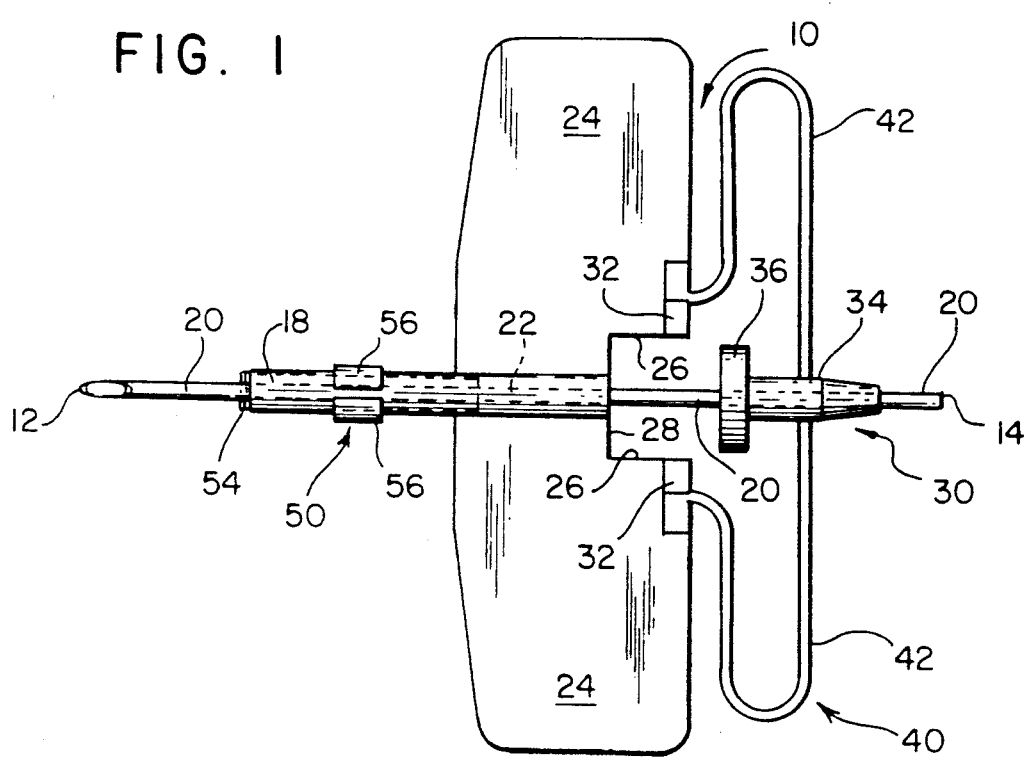
FIG. 1 is a top plan view of a preferred embodiment of the invention showing the needle assembly prior to use.

Referring to the drawings, FIGS. 1–4 show a preferred embodiment of the invention incorporating the unique features and basic concepts thereof. The same embraces a guide member 10 for effecting primary shielding of needle 20, a manipulating member 30 disposed rearwardly of the guide member 10, and interconnecting means 40 between the guide member and the manipulating member, the cooperation of which will be set forth more fully hereinafter. Also, as further explained, the members 10, 30, and 40 are preferably molded, as by injection molding, as a single integral unit-handled assembly.

Thus, a generally conventional metal needle cannula 20 includes the usual beveled and sharpened tip 12 at its distal end and a remote proximal end 14 which is connected to medical tubing (not shown) in known manner. Alternatively, medical tubing could be affixed to the enlarged proximal end of manipulating member 30. Surrounding needle 20 is the guide member and primary needle shielding component 10 which includes central tubular portion 18 having a bore or passageway 22 therethrough within which is slidably received needle 20. Tubular member 18 is of extended length so as to embrace a significant length of needle 20 to adequately guide and support the same.

Formed integrally with tubular portion 18 and extending laterally thereof on either side are generally planar and flexible wing-like sections 24. The wings 24 are formed at 26 to define a pocket or recess 28, and the wing proximal portions thereadjacent are provided with upstanding lugs or flanges 32.

While needle 20 is normally free to slide within passageway 22 of guide member 10, the manipulating member 30 includes a tubular base member 34 which is bonded securely to the periphery of needle 20 near its proximal end so as to be rigid therewith, whereby manual movement of the base member 34 alone will effect like movement therewith of the needle.

Manipulating member 30 has at its end a radially enlarged flange 36 for interengaging cooperation with the flanges 32 of wings 24 when in mutually generally axially aligned condition, as set forth hereinafter.

Interconnecting and restraint means 40 between guide member 10 and manipulating member 30 are provided, namely flexible loop-like strap portions 42. The straps 42 as shown in FIG. 1 are respectively fixedly connected at their ends, as by integral molding, to wings 24 adjacent flanges 32 and to the base member 34. Irrespective of the particular points or nature of connection, the straps are precisely dimensioned with respect to the length of needle 20, guide member 10 and manipulating member 30 for a purpose noted hereinafter.

Another alternative form of the invention is illustrated in FIG. 22 in which the interconnecting and restraint means between guide member 10 and manipulating member 30 is formed integrally with only one of these two members. In FIG. 22, for example, the restraint means is formed integrally with guide member 10 and has a loop 43 at its proximal end that encircles the conically shaped proximal end of manipulating member 30. The loop is of such a diameter that it fits onto the proximal end of manipulating member 30 so that it cannot slide off the distal end of manipulating member 30 and thereby limits the separation of the manipulating member 30 from the guide member 10 during needle withdrawal in accordance with this invention, as set forth hereinafter.

Figure 2:
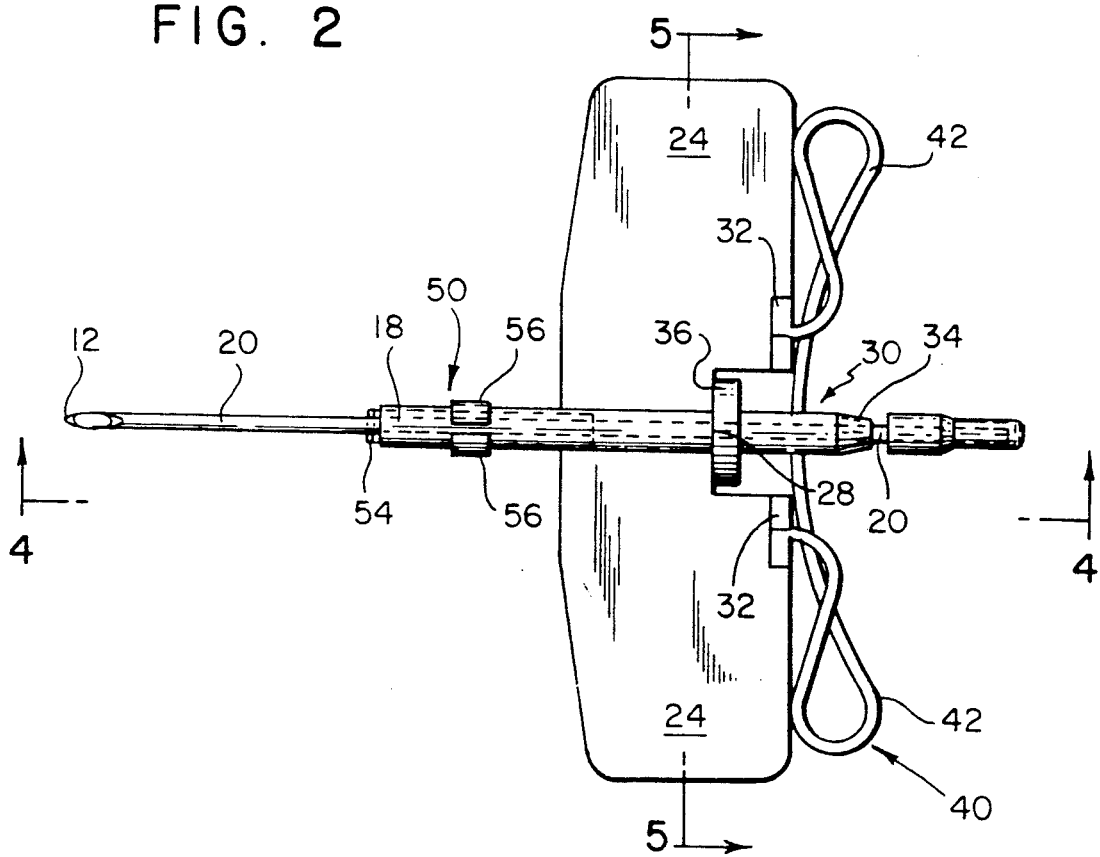
FIG. 2 is a plan view similar to FIG. 1 but wherein the needle has been advanced relative to the guide means.
Figure 3:
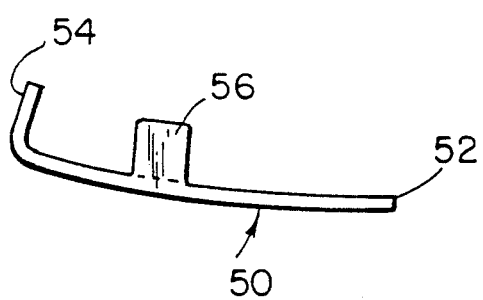
FIG. 3 is a side elevation of an illustrative leaf spring of a needle blocking and securing means.
Figure 5:
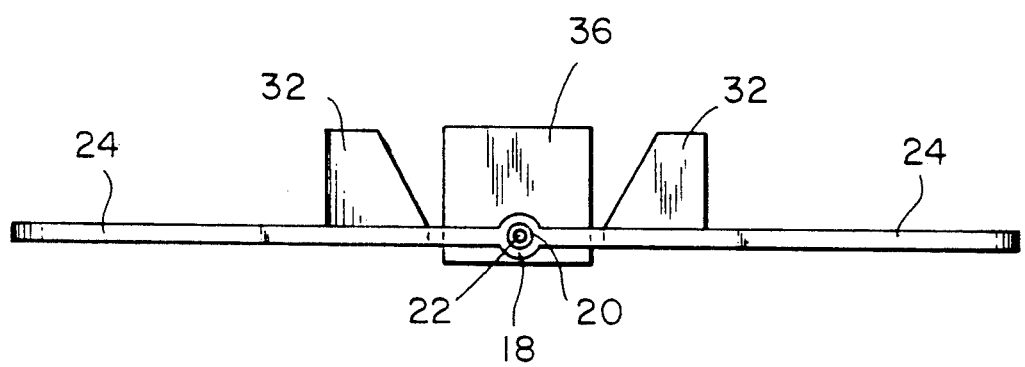
FIG. 5 is a frontal sectional view on the lines 5—5 as shown in FIG. 2.
Figure 6:
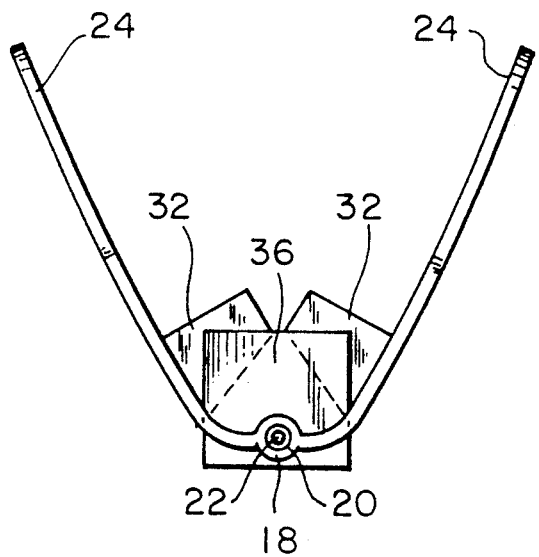
FIG. 6 is a frontal sectional view as in FIG. 5 but with the wing sections of the guide member flexed to the guide member/manipulating member interengaging position.

Importantly, in the embodiment of FIGS. 1-4, tubular member 18 carries a needle point shield and guard device 50, seen alone in FIG. 3, which comprises in its neutral and relaxed position a curved leaf spring of steel or the like having an axially extending leg 52, a generally right-angled blocking plate 54, and a pair of clip legs 56 forming a gripping collar for securely holding the guard device 50 onto the guide member 10.

In the form of FIGS. 1 and 2, and as seen in FIG. 4, the blocking plate 54 normally bears against needle 20 and thus is flexed against its initial curve as fabricated, as seen in FIG. 3, to maintain a spring force bias at all times toward shifting transversely of the tubular member 18.

Figure 12:
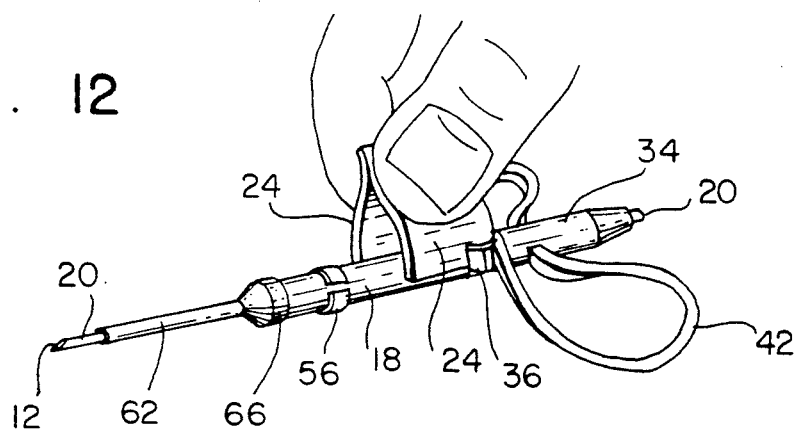
FIG. 12 is a view similar to FIG. 2 but utilizing a catheter in conjunction with a needle; perspective view thereof with the wings flexed at the time of tissue penetration.
Figure 13:
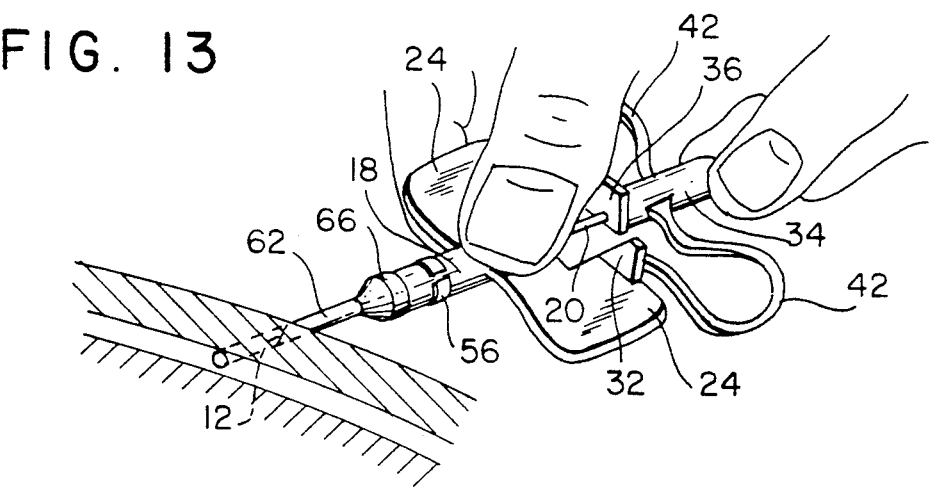
FIG. 13 is a perspective view of the devise of FIG. 11 and FIG. 12 but with the wings returned to substantially planar position for needle withdrawal and shielding.

Assembled and ready for use, the needle 20 is initially slightly advanced by forward movement of base member 30, the needle sliding forwardly in guide member 10, the base member flange 36 moving into the recess 28 forwardly of the wing flanges 32. Thereupon, the wings 24 are flexed upwardly and gripped by opposing fingers to substantially a vertical position thereby to hold firmly the needle for insertion into tissue. While pertaining to a modified form of the invention, FIGS. 12 and 13 illustrate the gripping action applicable to all forms of the invention which utilize wings 24 for needle insertion.

With the device so held, as in FIG., the guide member, manipulating member, and needle move as a unit in inserting the needle into the skin. After needle insertion as desired, the wings are released to lie substantially flat as in FIG. 13 and be free of the interfering relationship between flanges 32 and with flange 36 of the manipulating member 30.

Upon completion of the intravenous or other technique, to withdraw the needle from the biological tissue, the wings 24 are held generally against the skin with the fingers of one hand while the opposite hand is used to grasp base member 34, bonded to needle 20, and pull it away from the skin puncture site in a proximal direction.

Figure 7:
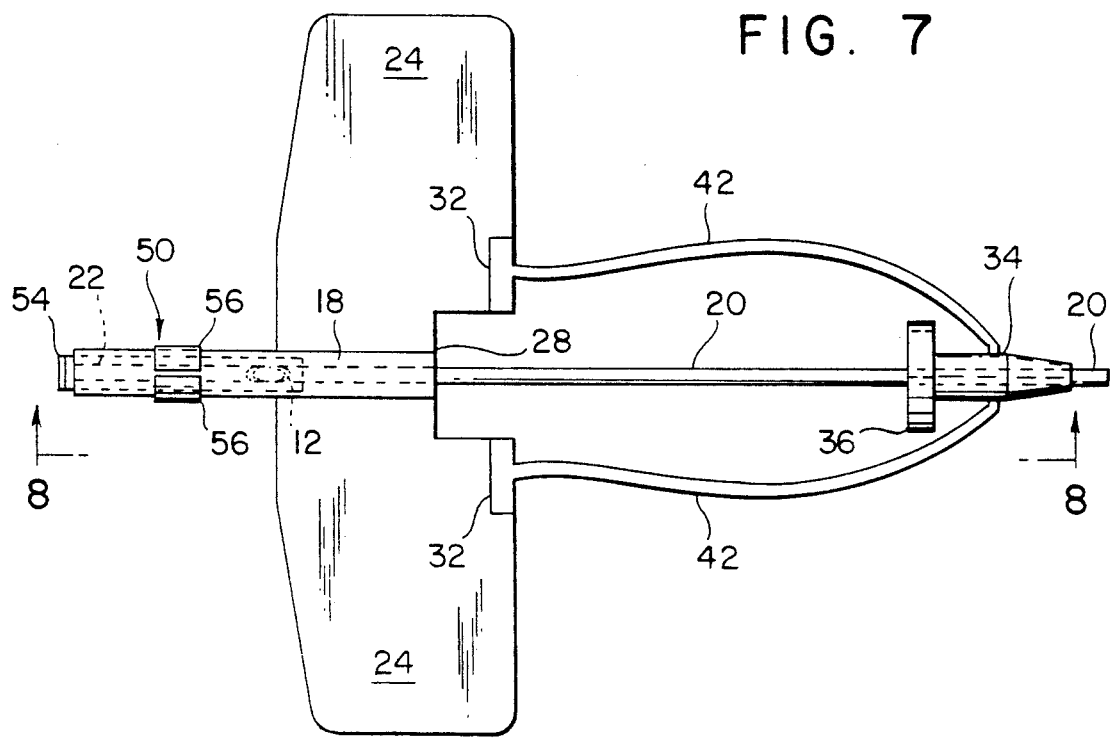
FIG. 7 is a top plan view similar to FIG. 1 but with the manipulating member fully retracted in a proximal direction with respect to the guide member to enclose and shield the needle.

In so doing, the needle 20 slides rearwardly in passageway 22, and in accordance with the invention, the interconnecting straps 42 are dimensioned to permit sufficient proximal movement of manipulating member 30 so as to withdraw the sharpened tip 12 of the needle fully into passageway 22 of the guide member 10, but not so far when fully extended as to permit the needle to be withdrawn from or even closely approach the proximate end of passageway 22 at recess 28, as clearly seen in FIGS. 7 and 8.

Upon withdrawal of the needle tip into the guide member, in the form of the invention in FIGS. 1-4, and FIG. 11, spring 50 is no longer restrained, and blocking plate 54 thereof snaps across the distal end of passageway 22 prevent any hazardous egress of the tip whatsoever, as seen in FIG. 8. As is evident, the configuration of plate 54 will control whether the entire passageway is blocked, or merely sufficient to prevent access to the contaminated needle tip. In like manner, the axial location of the spring guard 50 on tubular portion 18 will control just how close the plate 54 will be to the distal end of the passageway. In any event, under any circumstance, the contaminated needle tip 12 is fully shielded and the tissue-puncturing distal length of needle 20 is enclosed within the guide member 18.

It will be recalled that the guide member 10 and indeed the entire operative assembly is injection molded in one preferred embodiment from suitable polymeric material, as nylon, polyvinyl chloride, polypropylene or the like.

Depending on the characteristics of the plastic material as well as dimensional parameters of the wall of tubular portion 18 and the strength of guard spring 50, withdrawal of the needle 20 well into the passageway and thereby removal of the radial support for the tube provided by the needle may permit transverse flexure of the tubular portion 18 to secure further the needle point from unwanted access or egress.

Figure 9:
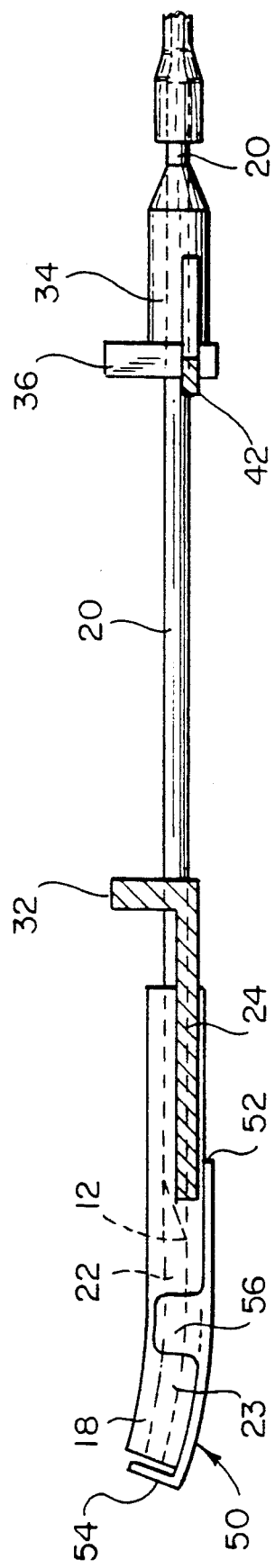
FIG. 9 is similar to FIG. 8 but wherein the guide member is of somewhat more flexible material.

This aspect of the invention is see FIG. 9 which corresponds to FIG. 8 with the needle withdrawn, but wherein the combination of spring strength and flexure characteristics of the plastic tube cause the same to bend laterally or transversely, whereby potential egress of the needle tip from the passageway is blocked not only by the plate 54 but also primarily by the curve in tubular portion 18. In this regard it is further noted that the conventional bevel of the needlepoint at 12 is oriented as shown in FIG. 9 on assembly with respect to the spring that any advancing movement of the needle in the bore passageway 22 would urge the point to bite into the bore sidewall 23 and be stopped and held thereby. In this form, the blocking plate 54 is optional and may be eliminated, keeping the spring otherwise to apply transverse pressure to the tube end.

Figure 10:
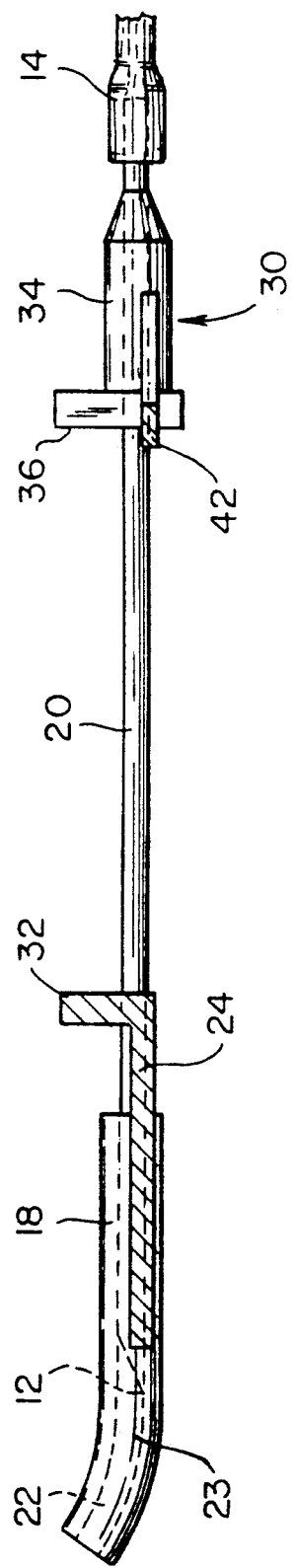
FIG. 10 is a view similar to FIG. 9 showing a modification of the invention.

A further modification of this concept is shown in FIG. 10 wherein the distal end of tubular portion 18 is initially formed from a plastic with shape memory characteristics and having an unstressed curvature as shown. Thus, the spring-like forces associated with the plastic component causing it to resume its original curved shape, which it had prior to assembly with needle cannula 20, result in the deflection of the unsupported distal end of tubular portion 18 following needle withdrawal therethrough whereby the needle tip 12 cannot emerge once withdrawn but bites into the curved tube wall 23 of passageway 22 to be held thereby if needle advance in the distal direction starts to occur.

Accordingly, in any form of the in the needle distal end section and especially the contaminated point are fully received within passageway 22 of guide member 10 and cannot be exposed therefrom whether distally or proximally, thereby obviating health hazards therefrom.

Figure 11:
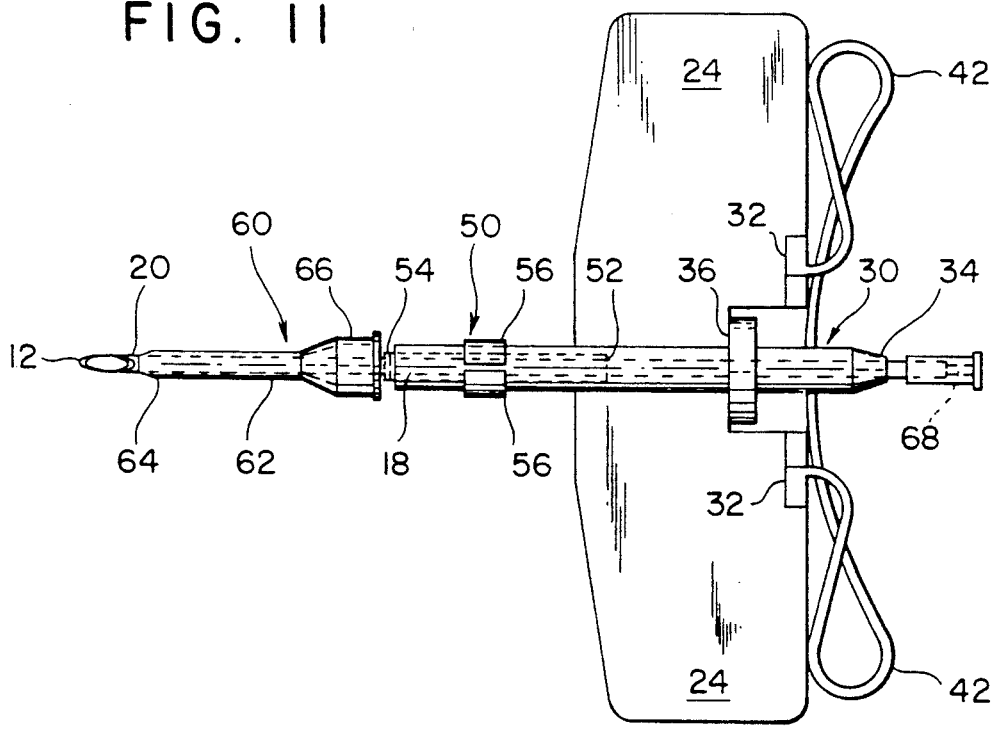
FIG. 11 is a view similar to FIG. 2 but showing a further form of the invention.

FIG. 11 illustrates a further form of the invention in which the cooperating guide member, manipulating member, interconnecting, and interengaging elements are as in FIG. 1-4, including the spring-urged guard 50, but wherein the same is particularly adapted for introduction of a catheter into a vein or the like. To this end, an over-the-needle intravenous catheter 60 is carried by the needle 20, which punctures the skin, the distal end of the soft catheter 60 placed into a blood vessel, and the entire emplacement assembly withdrawn leaving the catheter in place. A major portion 62 of the catheter fits snugly as a sleeve on the needle 20, terminating short of the beveled needle tip 12. The sleeve portion is preferably tapered at its distal end at 64 for ease of insertion. The proximal end of the catheter is a hub 66 enlarged to facilitate use as by connection to feeding or intravenous devices, and may be rather flexible or somewhat rigid.

In use, the assembly is operated as described in connection with FIGS. 1-4, and upon withdrawal of the needle, the distal end of the catheter remains implanted in the tissue, while the needle is safely captured as aforesaid. In like manner, the capture modes of FIGS. 9 and 10 be employed as well as that of FIG. 1.

In connection therewith, in order to determine proper needle location with respect to a blood vessel, the proximal end 14 of needle 20 instead of being connected to medical tubing is provided with a transparent or translucent vented chamber 68, whereby arrival of blood therein can be readily observed, after which the assembly is removed as described.

If desired, the blocking plate 54 of the spring 50 may be repositioned, and employed to bear against the hub 66 of the catheter instead of against the needle cannula proper, thereby retaining the catheter in association with the assembly. When the needle is withdrawn, radial support for the spring-biased plate 54 against hub 66 is removed, and the needle, guide member and manipulating member assembly can be taken away, the catheter 60 thereby becoming free to remain in the body.

Figure 14:
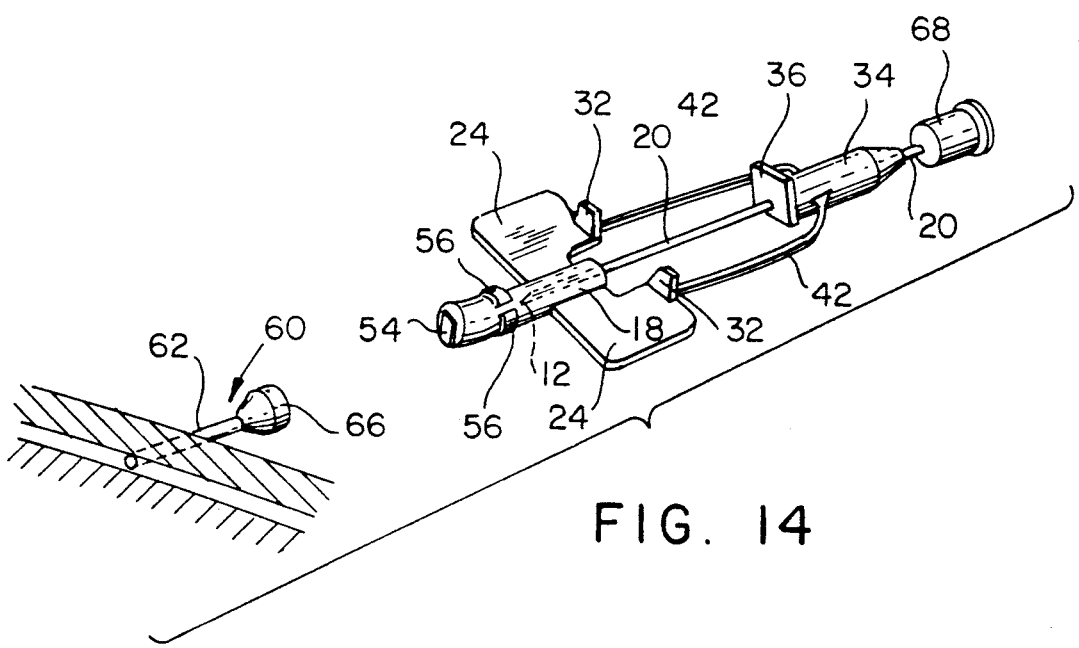
FIG. 14 is a perspective view thereof with the needle assembly withdrawn, the catheter remaining in situ, and the needle shielded.

In FIGS. 12-14, the invention in the form illustrated in FIG. 11 for intravenous catheter placement is shown in perspective view. These figures further illustrate the preferred method of using the device for needle insertion, catheter placement, and safe withdrawal and disposal. Note that catheter 62 fits snuggly on needle cannula 20 and is easily removed from same after the desired position in the blood vessel is obtained.

Figure 15:
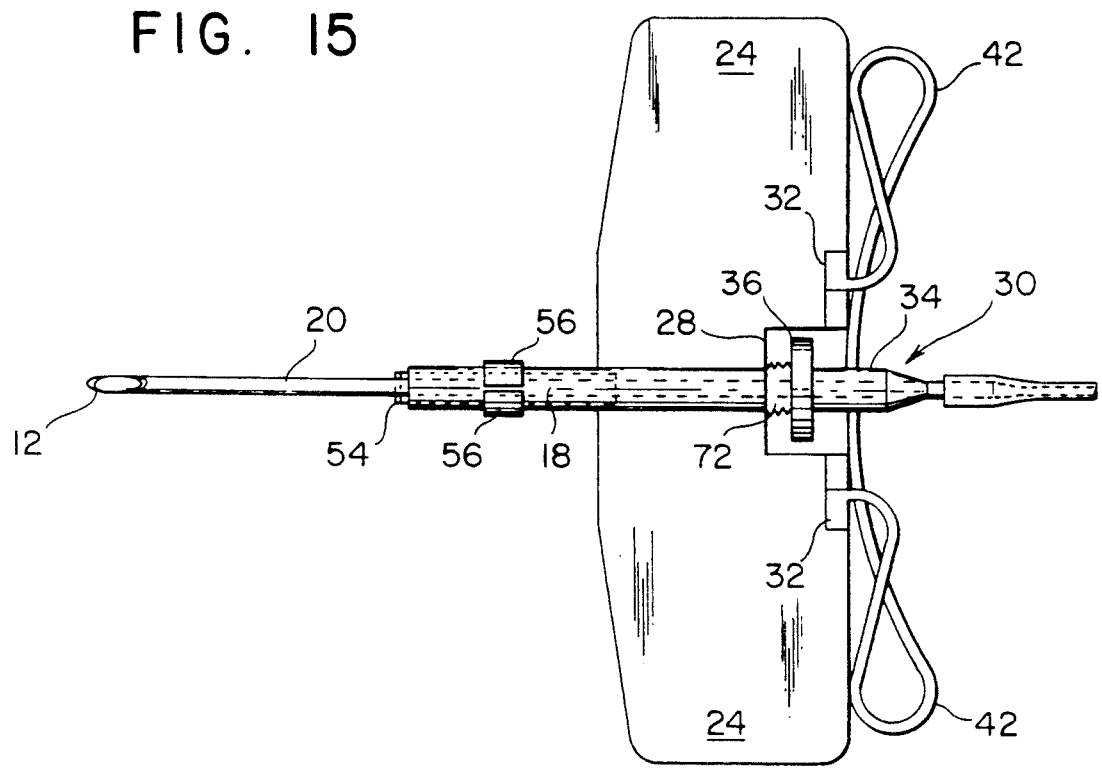
FIG. 15 is a top plan view similar to FIG. 1 of a further modified form of the invention.
Figure 16:
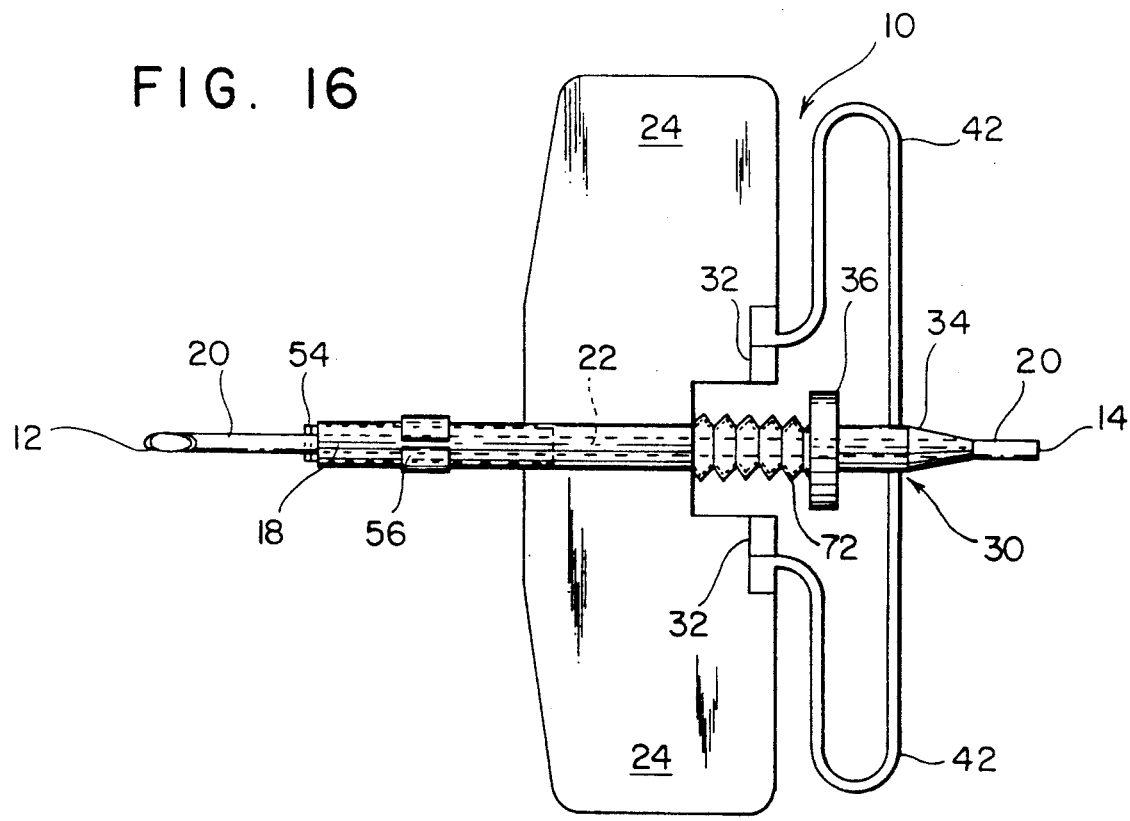
FIG. 16 is a top plan view similar to FIG. 15 of the further modified form of the invention in a different position.
Figure 17:
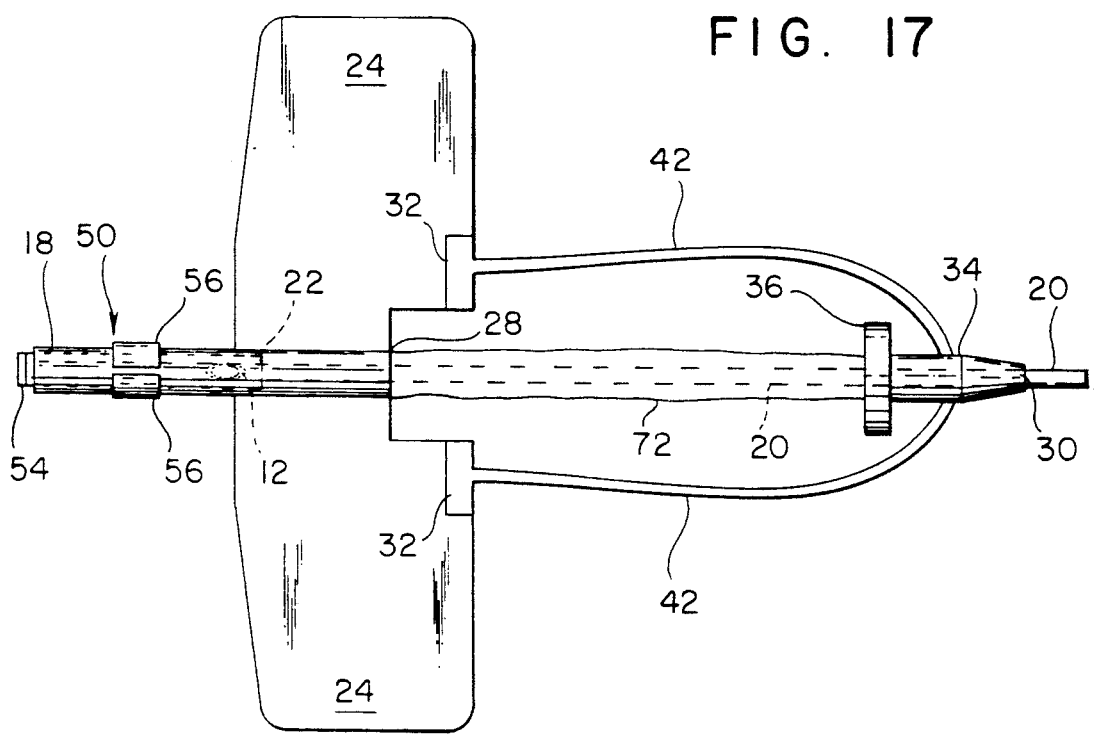
FIG. 17 is a top plan view similar to FIG. 16 of the further modified form of the invention showing the used needle in a fully withdrawn position with the entire needle covered.

Yet another modification of the invention appears in FIGS. 15-17 wherein a bellows-like expandable plastic sheath 72 is associated with the assembly of FIGS. 1-4 or FIG. 11. As shown, sheath 72 is disposed in recess 28, connecting the proximal end of wings 24 with the flange 36 of the manipulating member 30, being affixed to both. Accordingly, as the needle 20 is withdrawn progressively as seen in FIGS. 16 and 17, the sheath elongates and shields the incrementally exposed portion of needle 20, thereby providing further protection to healthcare workers against any hazaradous contamination as tissue debris on middle or rearward reaches of needle 20 that may possibly have occurred.

Figure 18:
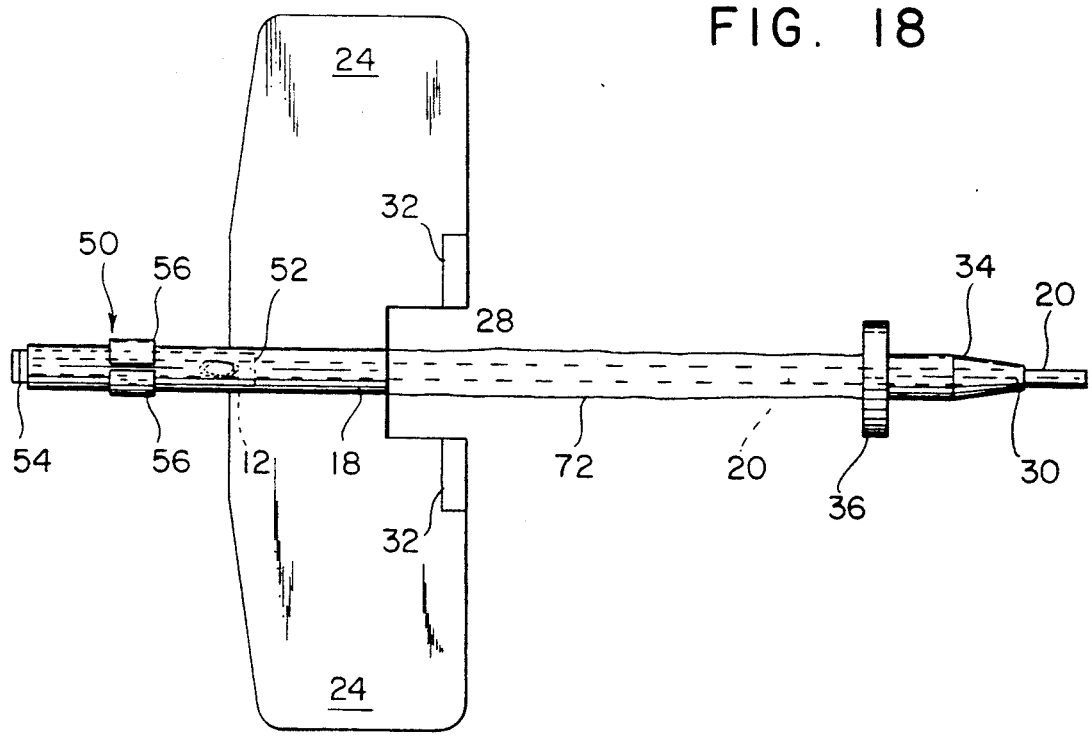
FIG. 18 is a top plan view similar to FIG. 17 of another modified form of the invention.

A further variant appears in FIG. 18 wherein the expansible sheath is employed as the interconnecting means in lieu of the straps 40, which are eliminated. In this form of the invention, untoward proximal removal of the needle is prevented by the full extension of the sheath 72, which is dimensioned to be less than that required to permit the needle point to emerge from the proximal end of guide member 10 and puncture the sheath.

Figure 19:
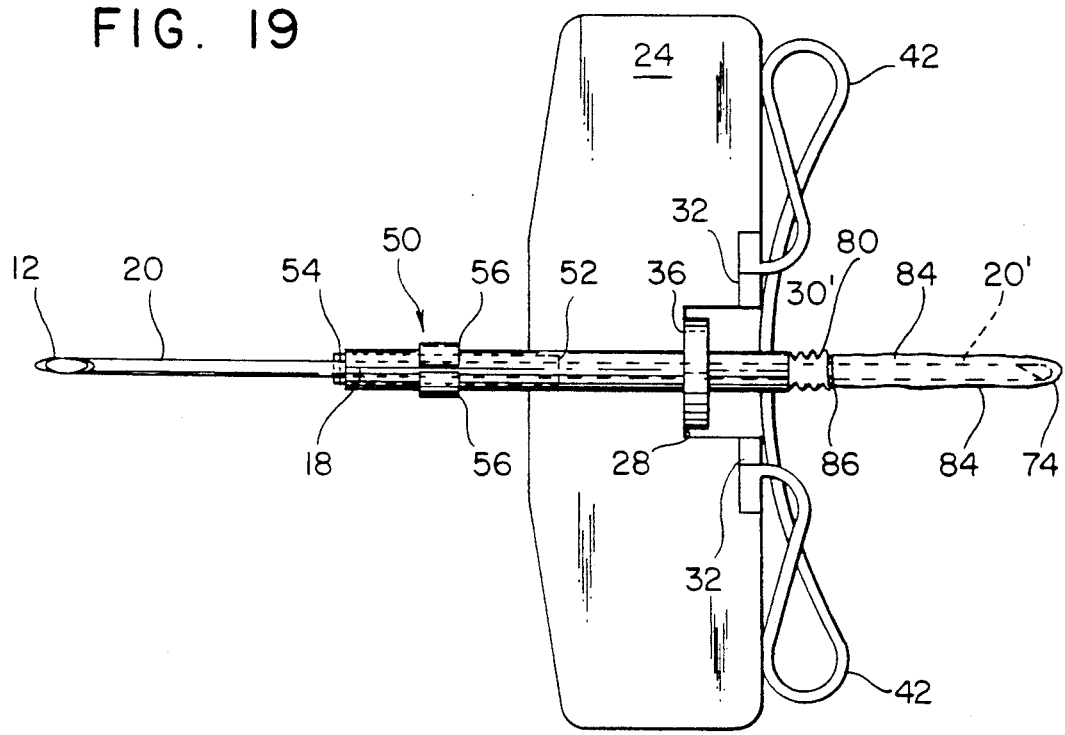
FIG. 19 is a to plan view similar to FIG. 2 of a fifth modified form of the invention adapted for blood collection.
Figure 20:
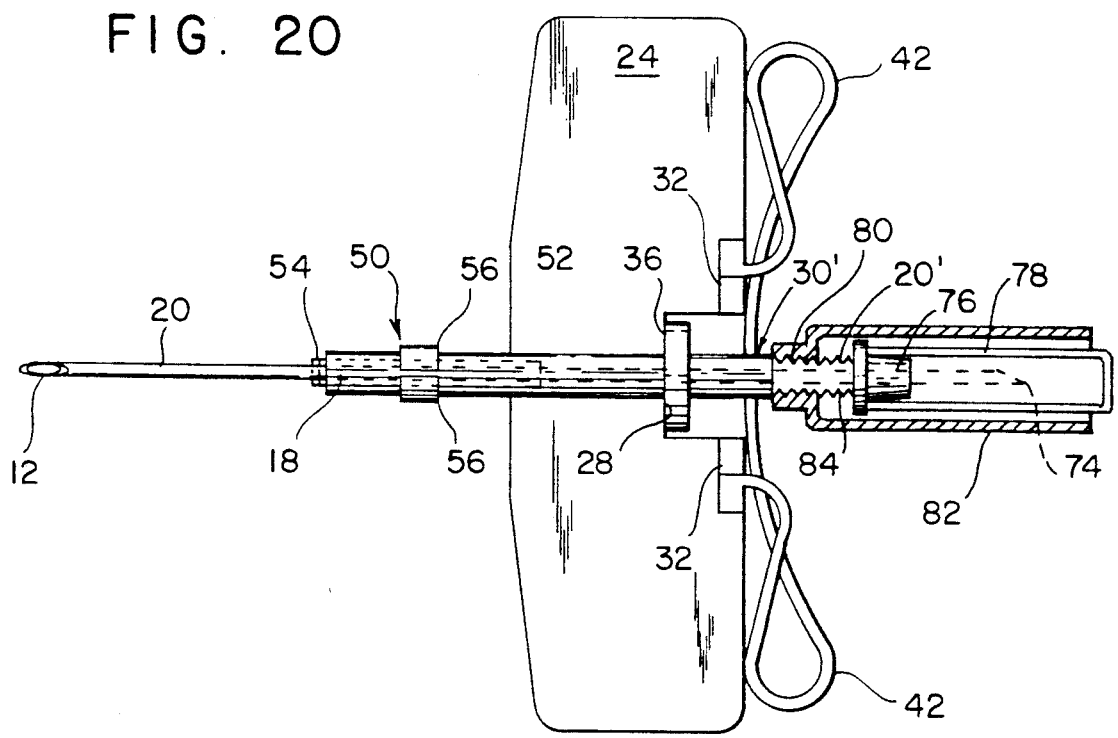
FIG. 20 is a to plan view similar to FIG. 19 of the fifth modified form of the invention when in use for blood collection.

FIGS. 19 and 20 illustrate a modification of the invention adapting the same for use with standard blood collection tubes. Thus the modified needle 20' therewith is a double-ended needle including proximal needle point 74 of usual nature for puncturing the rubber stopper 76 of standard blood collection tubes 78.

The modified base member 30' is provided with a proximal threaded extension 80 to which a conventional tube holder 82 is firmly threaded, thereby connecting the tube holder 82 fixedly with needle 20'0 bonded to manipulating member 30'. The tube holder also serves to shield medical personnel from the needle point 74 as well as aid in manipulation of the assembly in inserting the distal end 12 of the needle 20' into the flesh.

Additionally, a conventional flexible sheath of rubber or the like at 84 to facilitate taking sequential blood samples, encloses the proximal end of needle 20' and the point thereof and is secured to the threaded member 80 at 86.

Accordingly, upon insertion of a collection tube 78 into tube holder 82, the point 74 will puncture the rubber cap 76, sliding the sheath 84 in a distal direction as seen in FIG. 20, all as in current blood collection practices. As before, upon removal from tissue, the needle distal 12 is captured and shielded in passageway 22.

A further modification of this invention is similar to that illustrated in FIG. 19 except that the proximal needle assembly is adapted to fit with the standard hypodermic syringe instead of the blood collection tube holder. In this case, as shown in FIG. 21, the manipulating member, 30" is designed to affix to a syringe. The proximal end 14' of needle 20" is dispose within manipulating member 30". The distal end 91 of syringe barrel 90 fits tightly with manipulating member 30" as shown so that the interior chamber 92 of syringe barrel 90 is in fluid communication with the interior passageway of needle cannula 20".

In the modifications shown in FIGS. 19 and 21, needle insertion into tissue may be accomplished either while gripping wings 24 as described hereinabove or while holding the blood collection tube holder 82 or syringe barrel 90, respectively. When needle insertion is carried out while gripping the tube holder 82 or syringe barrel 90, the need for flanges 32 and 36 is obviated. The overall shape of the guide means and straps 42 may be modified as well to further provide design efficiency and to simplify manufacture.

Figure 23:
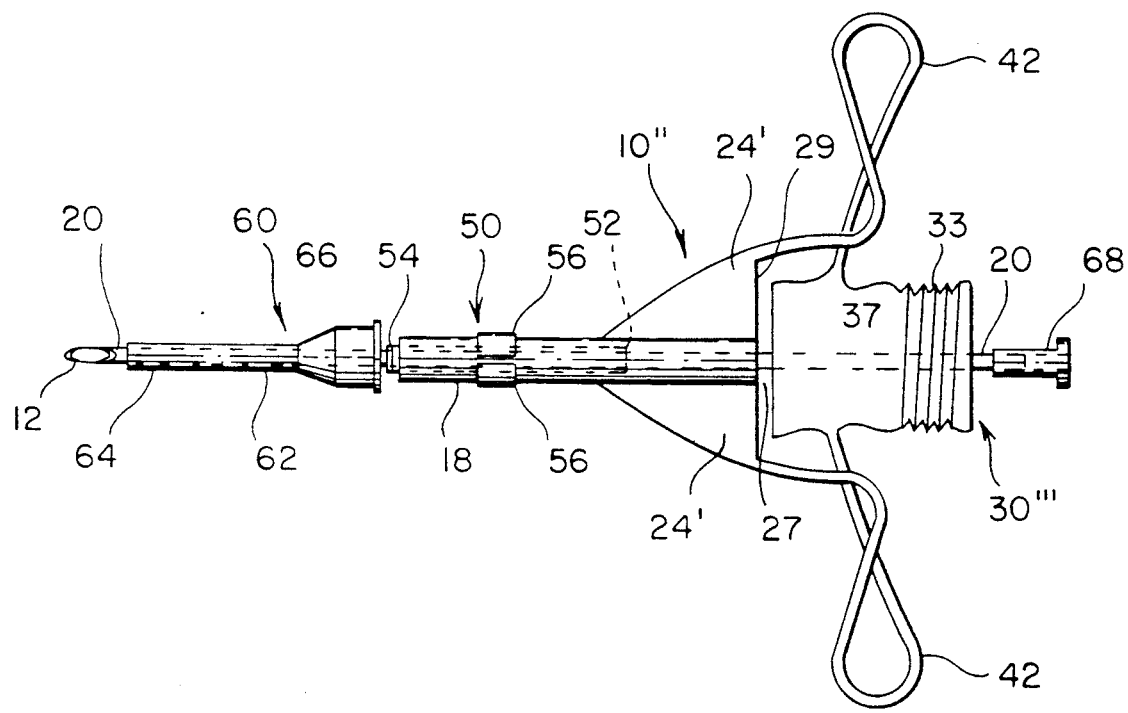

FIG. 23 illustrates another preferred embodiment of the invention in which modified manipulating member 30''' provides a textured surface 33 and has a somewhat hourglass shape to facilitate finger gripping. Mechanical interaction between guide member 24' and manipulating member 30''' which latter is as before bonded to needle cannula 20, is confined to a separable abutment zone 27 between the members and by the interconnecting straps 42.

In this embodiment, member 30''' is gripped for insertion of needle tip 12 into biological tissue, during which insertion the distal end 37 of member 30''' abuts directly the proximal end 29 of guide member 10'' so that the two members move together during insertion. During needle withdrawal, leaving catheter 60 in desired position within the blood vessel, member 10'' is held in position at the skin puncture site while member 30''' is pulled away therefrom to the limit permitted by straps 42, thus retracting needle tip 12 into tubular segment 18 of member 10'', and the needle guard or shield means as at 54 (or the other means disclosed) operates as heretofore. In this form of the invention it will be seen that wings 24' are of reduced size and are not flexed in the manner previously shown, not having the interengagable abutments thereon.

It follows that it is a feature of the invention that, during needle insertion, the device could be used with either the separable non-interlocking interaction of the guide member and manipulating member as shown in FIG. 23, or the interengagable form as illustratively shown in FIG. 12.

While we have disclosed preferred and variant forms of our invention, it will be evident that the concepts, structure and features thereof may be utilized in other environments and arrangements without departing from the spirit and scope of the invention as defined in the appended claims.

What is claimed is:

1. A disposable medical needle assembly having facile insertion and full enclosing and shielding means for the needle comprising:
   a needle having a point at its distal end,
   needle insertion and retraction means cooperatively associated with said needle for maintaining a distal portion of said needle exposed for insertion into the body, and including:
   (a) needle guide means in the form of a tubular member slidably carrying said needle and for fully enclosing the said needle distal portion upon withdrawal thereof from the body and into said tubular member, and,
   (b) needle manipulating means secured to said needle and fixed with respect thereto,
   (c) abutment means cooperatively associated with said guide means and said manipulating means to preclude relative movement between said guide means and said needle during insertion thereof, said abutment means being releasable to permit said relative movement upon needle withdrawal, said tubular member being disposed between said needle manipulating means and the distal end of said needle,
   said abutment means including releasably interengagable elements respectively carried by said guide means and said manipulating means,
   said interengagable elements include portions respectively carried by said guide means and said manipulating means for movement relative to each other between a first position in which said portions are in a position to engage each other and a second position in which said portions are in a position to preclude engagement therebetween,
   said guide means portion having flexible wing-like sections carried by said tubular member and which are capable of flexing between said first portion and said second position,
   said manipulating means having distal surfaces thereon and said guide means wing-like sections having proximal surfaces thereon for respective engagement in said first portion, and,
   shield means for said needle point, said means being operative for automatically precluding access to and preventing extension of said needle from said tubular member when said needle is withdrawn thereinto.

2. The disposable medical needle assembly of claim 1 wherein said surfaces are flanges carried respectively by said wing-like sections and said manipulating means.

3. The disposable medical needle assembly of claim 1 further including a flexible extensible sleeve enclosing said needle between said guide means and said manipulating means to preclude contamination therefrom.

4. The disposable medical needle assembly of claim 1 further including connection means proximal of said manipulating means for a blood collection tube holder, and wherein said needle includes a needle point proximal end for blood collection tubes.

5. The disposable medical needle assembly of claim 1 wherein said needle point shield means is cooperatively associated with the distal end of said guide means tubular member through which said distal end portion of said needle extends when in use.

6. The disposable medical needle assembly of claim 5 wherein said needle point shield means includes a tip guard element, and,
   means for moving said tip guard element from a retracted position free of blocking said needle when said needle is extended to a blocking position with respect to said needle when said needle is retracted within said tubular member, thereby to prevent exposed access to said needle tip.

7. The disposable medical needle assembly of claim 6 wherein said guard element engages said needle when said needle is extended, and wherein said moving means is normally tensioned to urge said guard element against said needle and toward said blocking position while said needle is exposed,
   whereby retraction of said needle into said guide means frees said guard element from contact with said needle and permits said spring to move said guard member into blocking position.

8. The disposable medical needle assembly of claim 7 wherein said moving means is a spring.

9. The disposable medical needle assembly of claim 8 wherein said spring is a leaf spring having ear means at its proximate end for securement to said guide means and carries said guard element at its distal end and disposed immediately forwardly adjacent to the distal end of said guide means.

10. The disposable medical needle assembly of claim 9 wherein said guard is a flexible distal portion of said guide means tubular member, and is transversely deflected by said spring when said needle is withdrawn therepast, thereby to preclude movement in an axial distal direction by said needle.

11. The disposable medical needle assembly of claim 7 wherein said guide means includes a resilient polymeric distal portion having a preformed transversely directed curved configuration, and said moving means is the biasing stress imparted to said distal portion when said curved end is resiliently forced to a position coaxial with said needle when said needle extends therefrom, whereby when said needle is withdrawn into said guide member and past said distal portion, the latter resumes said curved configuration and is thereby no longer coaxial with said needle to preclude axial needle movement to extended position once withdrawn therefrom.

12. A disposable medical needle assembly having facile insertion and full enclosing and shielding means for the needle comprising:

a needle having a point at its distal end, needle insertion and retraction means cooperatively associated with said needle for maintaining a distal portion of said needle exposed for insertion into the body, and including:

(a) needle guide means in the form of a tubular member slidably carrying said needle and for fully enclosing the said needle distal portion upon withdrawal thereof from the body and into said tubular member, and, (b) needle manipulating means secured to said needle and fixed with respect thereto, (c) abutment means cooperatively associated with said guide means and said manipulating means for engagement to preclude relative separating movement between said guide means and said needle during insertion thereof, said abutment means being releasable to permit said relative movement upon needle withdrawal, and shield means for said needle point for automatically precluding access to and preventing extension of said needle from said tubular member when said needle is withdrawn thereinto, and, said guide means and said manipulating means are interconnected by flexible strap means.

13. The disposable medical needle assembly of claim 12 wherein said guide means, flexible strap means, and said manipulating means are a unitary molded plastic element.

14. A disposable medical assembly, having cooperating elements for association with a needle, comprising:

guide means including a tubular member having a bore therethrough for slidable reception of a needle therein, manipulating means including a base portion for securement to a needle, said guide means and manipulating means being relatively movable between a first position with said guide means and manipulating means abutting one another so as to preclude separating movement between said guide means and manipulating means with the needle extended from said guide means, and a second position wherein said guide means and manipulating means are free of abutment and relatively spaced from one another with said needle withdrawn into said guide means, said guide means including flexible wing-like sections cooperatively associated with said guide means and said manipulating means in said first position, means preventing distal emergence of the needle from said guide means after retraction thereof into said guide means, and, a pair of flexible straps respectively connected between said guide means and said manipulating means.

15. The disposable medical needle assembly of claim 14 further including tubular means for flexibly interconnecting said guide means and manipulating means.

16. The disposable medical needle assembly of claim 15 wherein said guide means and said flexible tubular interconnecting means are unitarily molded from plastic.

17. The disposable medical needle assembly of claim 15 wherein said manipulating means and said flexible tubular interconnecting means are unitarily molded from plastic.

18. The disposable medical needle assembly of claim 15 wherein said guide means, manipulating means and said flexible tubular interconnecting means are unitarily molded from plastic.

19. The disposable medical needle assembly of claim 15 wherein said tubular flexible interconnecting means is a flexible tubular extensible sleeve enclosing said needle between said guide means and said manipulating means to preclude contamination therefrom.

20. A disposable medical assembly comprising:

guide means having a bore for slidably receiving a needle therein with the distal end thereof projecting forwardly therefrom, manipulating means proximal to said guide means and bonded to a proximal portion of a said needle, whereby movement of said manipulating means relative to said guide means moves said needle with respect to said guide means.

abutment means for preventing separating movement of said guide means and said manipulating means when said needle is projected forwardly, said guide means including flexible wing-like sections for cooperatively associated with said abutment means, flexible strap means extending between said guide means and said manipulating means for limiting separating movement of said manipulating means with respect to said guide means so as to preclude proximal withdrawal of said needle from said guide means, and permitting sufficient separating movement to retract the distal end of said needle fully within said guide means, and, means preventing distal emergence of the needle from said guide means after retraction thereof into said guide means.

21. The disposable medical needle assembly of claim 20 wherein the said energized preventing means includes means for obturating the guide means bore.

22. The disposable medical needle assembly of claim 20 wherein the said energized preventing means includes means for altering the configuration of said bore.

* * * * *

UNITED STATES PATENT AND TRADEMARK OFFICE
CERTIFICATE OF CORRECTION

PATENT NO. : 5,176,655
DATED : January 5, 1993
INVENTOR(S) : McCormick et al

It is certified that error appears in the above-identified patent and that said Letters Patent is hereby corrected as shown below:

Claim 1, in Column 10, lines 13 and 18, in
both lines, "portion" should read "position"

Signed and Sealed this

First Day of February, 1994

Attest:

BRUCE LEHMAN

*Attesting Officer*          *Commissioner of Patents and Trademarks*